United States Patent
Boulens et al.

(10) Patent No.: US 9,428,531 B2
(45) Date of Patent: Aug. 30, 2016

(54) CYCLIC NICKEL-BASED COMPLEXES AND THEIR USE IN A PROCESS FOR THE TRANSFORMATION OF OLEFINS

(71) Applicants: IFP Energies nouvelles, Rueil-Malmaison (FR); Universiteit Van Amsterdam, Amsterdam (NL)

(72) Inventors: Pierre Boulens, Lyons (FR); Pierre-Alain Breuil, Lyons (FR); Joost Reek, Amersfoort (NL); Helene Olivier-Bourbigou, Saint Genis-Laval (FR)

(73) Assignees: IFP Energies nouvelles, Rueil-Malmaison (FR); Universiteit Van Amsterdam, Amsterdam (NL)

( * ) Notice: Subject to any disclaimer, the term of this patent is extended or adjusted under 35 U.S.C. 154(b) by 0 days.

(21) Appl. No.: 14/698,500

(22) Filed: Apr. 28, 2015

(65) Prior Publication Data
US 2015/0307537 A1    Oct. 29, 2015

(30) Foreign Application Priority Data
Apr. 28, 2014  (FR) .................................... 14 53818

(51) Int. Cl.
| | | |
|---|---|---|
| C07F 15/00 | (2006.01) | |
| C07F 15/04 | (2006.01) | |
| C07C 2/32 | (2006.01) | |
| B01J 31/18 | (2006.01) | |
| C07F 9/28 | (2006.01) | |
| C07C 211/65 | (2006.01) | |
| B01J 31/22 | (2006.01) | |
| B01J 31/24 | (2006.01) | |

(52) U.S. Cl.
CPC ............ *C07F 15/045* (2013.01); *B01J 31/188* (2013.01); *B01J 31/1845* (2013.01); *B01J 31/2247* (2013.01); *B01J 31/2256* (2013.01); *B01J 31/24* (2013.01); *C07C 2/32* (2013.01); *C07C 211/65* (2013.01); *C07F 9/28* (2013.01); *B01J 2231/20* (2013.01); *B01J 2531/0213* (2013.01); *B01J 2531/847* (2013.01); *C07C 2531/22* (2013.01)

(58) Field of Classification Search
CPC ........ C07F 15/04; C07F 9/28; C07C 211/65; C07C 2/32; B01J 31/18
USPC ......................................................... 556/139
See application file for complete search history.

(56) References Cited

U.S. PATENT DOCUMENTS

| 6,060,569 A | 5/2000 | Bennett et al. |
|---|---|---|
| 6,710,007 B2 * | 3/2004 | Brookhart ............. C07F 15/006 502/155 |
| 8,283,276 B2 | 10/2012 | Reek et al. |
| 2011/0003959 A1 | 1/2011 | Reek et al. |

FOREIGN PATENT DOCUMENTS

EP    2062906 A1    5/2009

OTHER PUBLICATIONS

Patureau, F. W. et al., "Supramolecular Hydrogen-Bonding Tautomeric Sulfonamido-Phosphinamides: A Perfect P-Chirogenic Memory," Eur. J. Inorg. Chem., 2012, pp. 496-503.
Terrade, F. G. et al., "Synthesis, Coordination Chemistry, and Cooperative Activation of H2 wit Ruthenium Complexes of Proton-Responsive METAMORPhos ligands," Eur. J. Inorg. Chem, 2014, pp. 1826-1835.
Peuckert, M. et al., "A new Nickel Complex for the Oligomerization of Ethylene," Organometallics, 1983, vol. 2, pp. 594-597.
French Search Report for FR-1453818 dated Jan. 15, 2015.

\* cited by examiner

*Primary Examiner* — Porfirio Nazario Gonzalez
*Assistant Examiner* — Kofi Adzamli
(74) *Attorney, Agent, or Firm* — Millen, White, Zelano & Branigan, P.C.

(57) ABSTRACT

The invention describes a novel type of nickel-based complex and its preparation method. The invention also concerns the use of said complex in a process for the transformation of olefins.

15 Claims, No Drawings

CYCLIC NICKEL-BASED COMPLEXES AND THEIR USE IN A PROCESS FOR THE TRANSFORMATION OF OLEFINS

The present invention relates to a novel family of nickel-based complexes and their preparation method. The invention also relates to the use of said complexes as catalysts for chemical transformation reactions.

PRIOR ART

The preparation of complexes based on transition metals for application thereof in various fields of chemistry is known, in particular in the field of catalytic transformations such as hydroformylation, hydrogenation, cross-coupling, olefin oligomerization, etc.

The preparation of complexes of this type depends on the choice of metal and on appropriate ligands. Among these ligands, bidentate ligands represent an important class of ligands used in the preparation of catalysts based on transition metals for various types of catalytic chemical transformations.

The document EP 2 220 099 B1 describes a system of coordination complexes comprising multidentate ligands with formula: $R_1-SO_2-NH-P(XR_2)_2$; or $R_1-SO_2-N=PH(XR_2)_2$, or $R_1-SO(OH)=NP(XR_2)_2$, in which X is independently O, S, NH, or a bond; in which $R_1$ and $R_2$ are independently selected from an alkyl group, which may or may not be substituted, and an aryl group, in which at least one equivalent of ligand is complexed with one equivalent of a metal selected from rhodium, iridium, platinum, palladium and the lanthanides. EP 2 220 099 B1 indicates that the coordination complex system may be used as a catalyst for hydroformylation, hydrogenation, polymerisation, isomerisation etc.

In its research, the Applicant has developed a novel family of nickel-based complexes and their preparation method. Surprisingly, it has been shown that such complexes have interesting catalytic properties. In particular, these catalysts have a good activity in the oligomerization of olefins.

One aim of the invention is to provide a novel family of nickel-based complexes. In another aspect, a novel catalytic system is proposed comprising said complexes for chemical transformation reactions, in particular for the oligomerization of olefins.

DETAILED DESCRIPTION OF THE INVENTION

Nickel Complexes

The complexes of the invention are nickel-based complexes with formula (I) or (II)

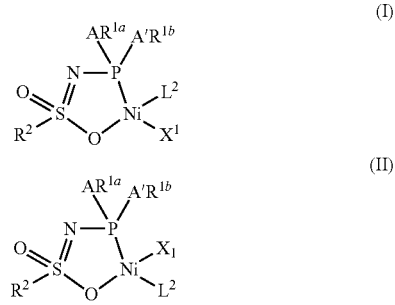

in which
the atoms P, N, S, O constitute a ligand fragment,
A and A', which may be identical or different, are independently O, S, $NR^3$ or a single bond between the phosphorus atom and a carbon atom,
the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements,
the groups $R^1$, represented in the formula by $R^{1a}$ and $R^{1b}$, with $R^{1a}$ and $R^{1b}$ being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group $R^2$ is selected from alkyl groups which may or may not be cyclic, which may or may not be substituted and which may or may not contain heteroelements, and aromatic groups which may or may not be substituted and which may or may not contain heteroelements,
$L^2$ represents a Lewis base,
$X^1$ is a hydrogen atom or a halogen or a carbon atom bonded to or forming part of at least one alkyl group, which may or may not be cyclic, which may or may not be unsaturated, which may or may not be substituted and which may or may not contain heteroelements, and an aromatic group which may or may not be substituted and which may or may not contain heteroelements,
$L^2$ and $X^1$ are such that the oxidation number of the nickel is respected.

In the context of the present invention, the term "alkyl" is intended to mean a linear or branched hydrocarbon chain containing 1 to 15 carbon atoms, preferably 1 to 10. Preferred alkyl groups are advantageously selected from methyl, ethyl, propyl, isopropyl, butyl, isobutyl and tert-butyl groups. These alkyl groups may be substituted with heteroelements or groups containing heteroelements, such as a halogen or an alkoxy group. The term "alkoxy" substituent means an alkyl-O— group in which the term "alkyl" has the meaning given above. Preferred examples of alkoxy substituents are methoxy or ethoxy groups.

The term "cyclic alkyl" means a monocyclic hydrocarbon group containing more than 3 carbon atoms, preferably 4 to 24, more preferably 6 to 12, preferably a cyclopentyl, cyclohexyl, cyclooctyl or cyclododecyl group, or a polycyclic (bi- or tricyclic) group containing more than 3 carbon atoms, preferably 4 to 18, such as adamantyl or norbornyl groups, for example.

The term "linear unsaturated alkyl" or "cyclic unsaturated alkyl" means a linear or cyclic alkyl group containing at least one unsaturated bond, the term "alkyl" and "cyclic alkyl" having the meaning given above.

The term "aromatic" means a mono- or polycylic aromatic group, preferably mono- or bicyclic, containing 5 to 20 carbon atoms. When the group is polycyclic, i.e. it comprises more than one cyclic ring, the cyclic rings may advantageously be condensed in pairs or connected in pairs via a bonds. The aromatic group in accordance with the invention may contain a heteroelement such as nitrogen, oxygen or sulphur.

The term "ligand" as used in the present invention is used indiscriminately to mean one or more of the limiting forms of the ligand with formula 1a), 1b) and/or 1c):

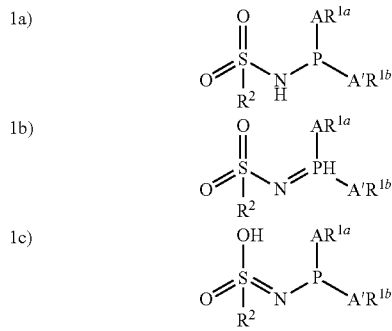

1a)
1b)
1c)

in which
A and A', which may be identical or different, are independently O, S, NR$^3$ or a single bond between the phosphorus atom and a carbon atom,
the group R$^3$ is either a hydrogen atom or an alkyl group, which may or may not be cyclic, which may or may not be substituted and which may or may not contain heteroelements, or an aromatic group, which may or may not be substituted and which may or may not contain heteroelements,
the groups R$^1$, represented in the formula by R$^{1a}$ and R$^{1b}$, with R$^{1a}$ and R$^{1b}$ being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group R$^2$ is selected from alkyl groups which may or may not be cyclic, which may or may not be substituted and which may or may not contain heteroelements, and aromatic groups which may or may not be substituted and which may or may not contain heteroelements.

The two groups R$^1$ (R$^{1a}$ and R$^{1b}$) may be identical or different. These two groups R$^{1a}$ and R$^{1b}$ may also be bonded together. In such a case, the two groups R$^1$ may correspond to groups such as bis-phenyl or bis-naphthyl.

The ligands of the invention may be prepared by a condensation reaction of a sulphonamide, for example para-n-butylphenyl-sulphonamide, and a phosphine halide such as Ph$_2$PCl, in the presence of a Brönsted base such as triethylamine, for example, in a solvent. In solution, these ligands may (co)exist in the three forms 1a), 1b) or 1c) described above.

L$^2$ represents a Lewis base. In the context of the present invention, the term "Lewis base" means any chemical entity a constituent of which has one or more free or non-bonding electron pairs. The Lewis bases of the invention in particular correspond to any ligand comprising an oxygen, nitrogen or phosphorus atom with a free or non-bonding electron pair or a π double bond which is capable of forming an η$^2$ type coordination with the nickel.

The group L$^2$ of the complex with formula (I) or (II) of the invention may represent a phosphine of the type P(A$^1$R$^{'1a}$)(A$^{'1}$R$^{'1b}$)(A$^{''1}$R$^{'1c}$) or a phosphinamine of the type (R$^{'1a}$A$^1$)(R$^{'1b}$A$^{'1}$)P—NH(R$^{'2}$) or (R$^{'1a}$A$^1$)(R$^{'1b}$A$^{'1}$)P—NH—S(O)$_2$(R$^{'2}$), in which:
A$^1$, A$^{'1}$ and A$^{''1}$, which may be mutually identical or different, are independently O, S, NR$^3$, or a single bond between the phosphorus atom and a carbon atom,
the group R$^3$ is either a hydrogen atom or an alkyl group, which may or may not be cyclic, which may or may not be substituted and which may or may not contain heteroelements, or an aromatic group which may or may not be substituted and which may or may not contain heteroelements,
the groups R$^{'1}$, i.e. R$^{'1a}$, R$^{'1b}$ and R$^{'1c}$, being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group R$^{'2}$ is selected from alkyl groups which may or may not be cyclic, which may or may not be substituted and which may or may not contain heteroelements, and aromatic groups which may or may not be substituted and which may or may not contain heteroelements.

X$^1$ is a hydrogen atom or a halogen or a carbon atom bonded to or forming part of at least one alkyl group which may or may not be cyclic, which may or may not be unsaturated, which may or may not be substituted and which may or may not contain heteroelements, and an aromatic group which may or may not be substituted and which may or may not contain heteroelements. Advantageously, X$^1$ is a hydrogen atom, an alkyl group which may or may not be cyclic, which may or may not be unsaturated, which may or may not be substituted and which may or may not contain heteroelements, or a halogen. When the group X$^1$ is a halogen, it may be a bromine, chlorine, iodine or fluorine atom.

In accordance with the invention, the groups R$^1$ i.e. R$^{1a}$ and R$^{1b}$, which may be identical or different and which may or may not be bonded together, and the groups R$^{'1}$, i.e. R$^{'1a}$, R$^{'1b}$ and R$^{'1c}$, which may be identical or different and which may or may not be bonded together, are independently selected from alkyl groups containing 1 to 15 carbon atoms and aromatic groups containing 5 to 20 carbon atoms, which may or may not be substituted and which may or may not contain heteroelements.

Preferably, the groups R$^1$, i.e. R$^{1a}$ and R$^{1b}$ which may be identical or different, which may or may not be bonded together, and the groups R$^{'1}$, i.e. R$^{'1a}$, R$^{'1b}$ and R$^{'1c}$, which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups, which may or may not be substituted and which may or may not contain heteroelements. In the case in which the groups R$^{1a}$ and R$^{1b}$, which may be identical or different, are bonded together, these groups may correspond to groups such as bis-phenyl or bis-naphthyl. In the case in which the groups R$^{'1}$, which may be identical or different, are bonded together, these groups may correspond to groups such as bis-phenyl or bis-naphthyl.

In accordance with the invention, the groups R$^2$ and the groups R$^{'2}$, which may be identical or different, are independently selected from alkyl groups containing 1 to 15 carbon atoms and aromatic groups containing 5 to 20 carbon atoms, which may or may not be substituted and which may or may not contain heteroelements.

Preferably, the groups $R^2$ and the groups $R'^2$, which may be identical or different, are independently selected from methyl, trifluoromethyl, ethyl, n-propyl, i-propyl, n-butyl, i-butyl, t-butyl, pentyl, cyclohexyl and adamantyl groups, which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain heteroelements.

Preferably, the group $R^3$ is either a hydrogen atom or an alkyl group.

The complex of the invention may be prepared by bringing at least one ligand comprising the ligand fragment constituted by the atoms P, N, S and O with formula (1a), (1b) or (1c) as defined in accordance with the invention, into contact with at least one precursor of nickel with an oxidation number of (0), a precursor of the group $X^1$, and optionally a Lewis base. The presence of a Lewis base is, for example, optional when a second equivalent of the ligand is employed. In this case, the ligand of the invention acts as a Lewis base. In a particular embodiment, the group $X^1$ may derive from the ligand itself.

The complex of the invention may also be prepared by bringing at least one ligand comprising the ligand fragment constituted by the atoms P, N, S and O with formula (1a), (1b) or (1c) as defined in accordance with the invention, into contact with at least one precursor of nickel with an oxidation number of (+II), in the presence of a reducing agent or a Brönsted base; and optionally a Lewis base. The presence of a Lewis base is optional, for example, when a second equivalent of the ligand is employed. In this case, the ligand of the invention acts as a Lewis base. In a particular embodiment, the group $X^1$ may derive from the nickel precursor with an oxidation number of (+II).

In the case in which a nickel precursor with an oxidation number (+II) is used in the presence of a reducing agent, any agent resulting in the reduction of nickel which is known to the skilled person may be used. The reducing agent may be selected from $NaBH_4$, $LiAlH_4$, $AlEt_3$, Na, K, $KC_8$ and dihydrogen.

In the case in which a precursor of nickel with an oxidation number of (+II) is used in the presence of a Brönsted base, any Brönsted base which is known to the skilled person may be used. The term "Brönsted base" means any molecular entity or corresponding chemical species which is capable of accepting a proton, such as triethylamine, for example.

The preparation temperature for the complexes of the invention may be in the range −80° C. to 130° C.

The complexes of the invention may be prepared in the presence or absence of a solvent. Preferably, the preparation is carried out in the presence of a solvent. The preparation solvent may be selected from organic solvents, in particular from ethers, alcohols, chlorine-containing solvents and saturated, unsaturated, aromatic or non-aromatic, cyclic or non-cyclic hydrocarbons. Preferably, the solvent is selected from hexane, cyclohexane, methylcyclohexane, heptane, butane or isobutane, monoolefins or diolefins preferably containing 4 to 20 carbon atoms, cycloocta-1,5-diene, benzene, toluene, ortho-xylene, mesitylene, ethylbenzene, dichloromethane, chlorobenzene, methanol, ethanol, pure or as a mixture, and ionic liquids. In the case in which the solvent is an ionic liquid, it is advantageously selected from the ionic liquids described in patents U.S. Pat. No. 6,951,831 B2 and FR 2 895 406 B1.

The complexes of the invention comprise a nickel with an oxidation number (+I) or (+II), preferably a nickel with oxidation number (+II). The complexes of the invention may also form multi-nuclear aggregates.

When the nickel precursor has oxidation number (0), it may be selected from nickel(0) bis(cycloocta-1,5-diene), nickel(0) bis(cycloocta-1,3-diene), nickel(0) bis(cycloocta-tetraene), nickel(0) bis(cycloocta-1,3,7-triene), bis(o-tolyl-phosphito) nickel(0)(ethylene), nickel(0) tetrakis(triphenyl-phosphite), nickel(0) tetrakis(triphenylphosphine) and nickel (0) bis(ethylene), used alone or as a mixture. Said nickel precursors may optionally be complexed with Lewis bases.

When the nickel precursor has oxidation number (+II), it may be selected from nickel (II) chloride, nickel(II)(dimethoxyethane) chloride, nickel(II) bromide, nickel(II)(dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate, for example, nickel(II) phenates, nickel(II) acetate, nickel(II) trifluoroacetate, nickel(II) triflate, nickel (II) acetylacetonate, nickel(II) hexafluoroacetylacetonate, allylnickel(II) chloride, allylnickel(II) bromide, methallyl-nickel(II) chloride dimer, allylnickel(II) hexafluorophosphate, methallylnickel(II) hexafluorophosphate, biscyclopentadienyl nickel(II), bisallyl nickel(II) and bismethallyl nickel(II); in their hydrated or non-hydrated form, used alone or as a mixture. Said nickel precursors may optionally be complexed with Lewis bases.

We shall now present some examples of complexes with formula (I) or (II) in accordance with the invention as well as the operating conditions by means of which they are obtained. These examples are given by way of illustration and do not in any way limit the scope of the invention.

Scheme 1 illustrates a complex of the invention with formula (I). Adding 2 equivalents of ligand L1, represented in its limiting form 1b), to one equivalent of $NiBr_2(DME)_2$ and triethylamine in benzene produces the complex C1 after 16 hours at 60° C. In this complex, the phosphorus atoms are in the cis position and $X^1$ corresponds to a bromine atom. The structure of the complex is characterized by X ray diffraction (XRD).

Scheme 1

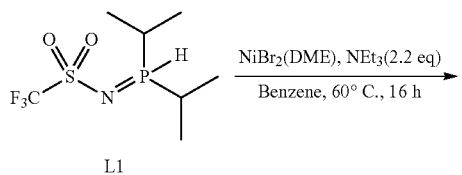

L1

-continued

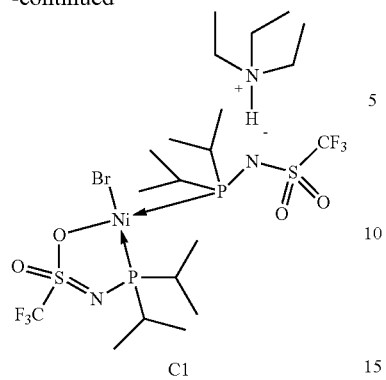

C1

Three complexes in accordance with the invention having formula (II) are illustrated in scheme 2. The addition of one equivalent of ligand L1 or L3, represented in the limiting form 1b), and one equivalent of tricyclohexylphosphine to one equivalent of nickel(0) bis(cycloocta-1,5-diene) in toluene respectively results in the production of complexes C2 or C3 after 3 hours and 16 hours respectively at 60° C. The addition of one equivalent of ligand L4, represented in its limiting form 1b), and one equivalent of tricyclohexylphosphine to one equivalent of nickel(0) bis(cycloocta-1,5-diene) (Ni(COD)$_2$) in toluene results in the production of complex C4 after 3 hours at 90° C.

In these complexes, the phosphorus atoms are in the trans position and $X^1$ corresponds to a hydrogen atom. The complexes are characterized in $^{31}P$ NMR by two split doublets with a large coupling constant $J_{PP}$ of the order of 230 Hz and two smaller coupling constants $J_{PH}$ corresponding to cis phosphorous-hydride coupling.

Scheme 2

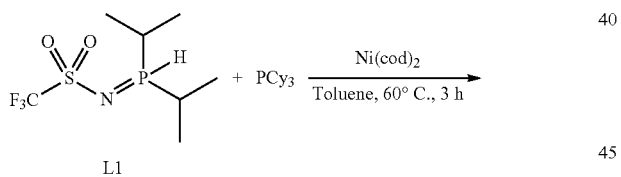

L1

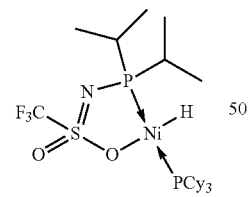

C2

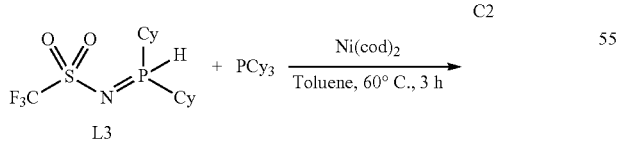

L3

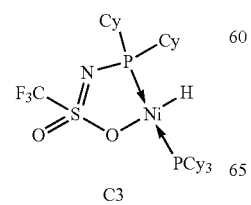

C3

-continued

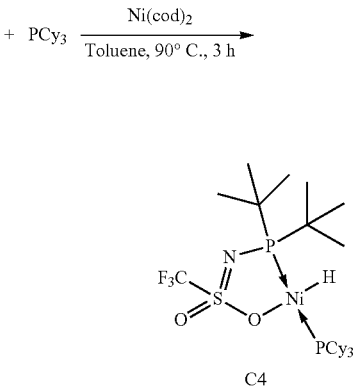

L4

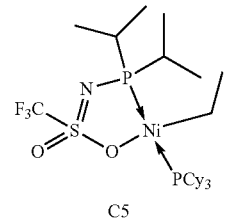

C4

Scheme 3 illustrates a complex of the invention with formula (II). Bubbling ethylene through for 3 h at atmospheric pressure into a mixture formed by one equivalent of ligand L1, PCy$_3$ and one equivalent of Ni(COD)$_2$ results in the formation of the complex C5.

Scheme 3

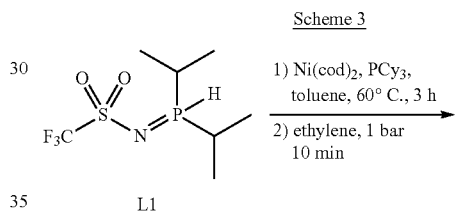

L1

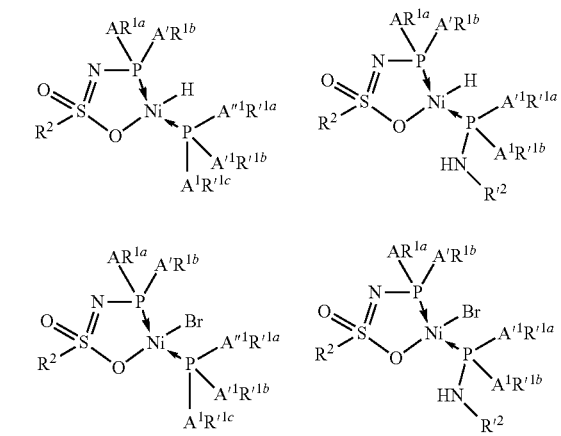

C5

Preferably, the complexes of the invention have the following formula (I) or (II):

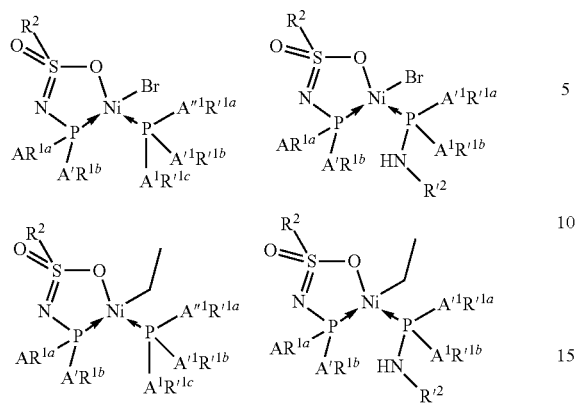
in which the nickel has oxidation number (+II) and A, A', A¹, A'¹, A"¹, R¹ᵃ, R¹ᵇ, R'¹ᵃ, R'¹ᵇ, R'¹ᶜ, R² and R'² have the meanings given in the context of the invention.
A non-exhaustive list of ligands which may be suitable for the preparation of the complexes of the invention is represented below. The ligands here are represented in their limiting forms 1a) and 1b).
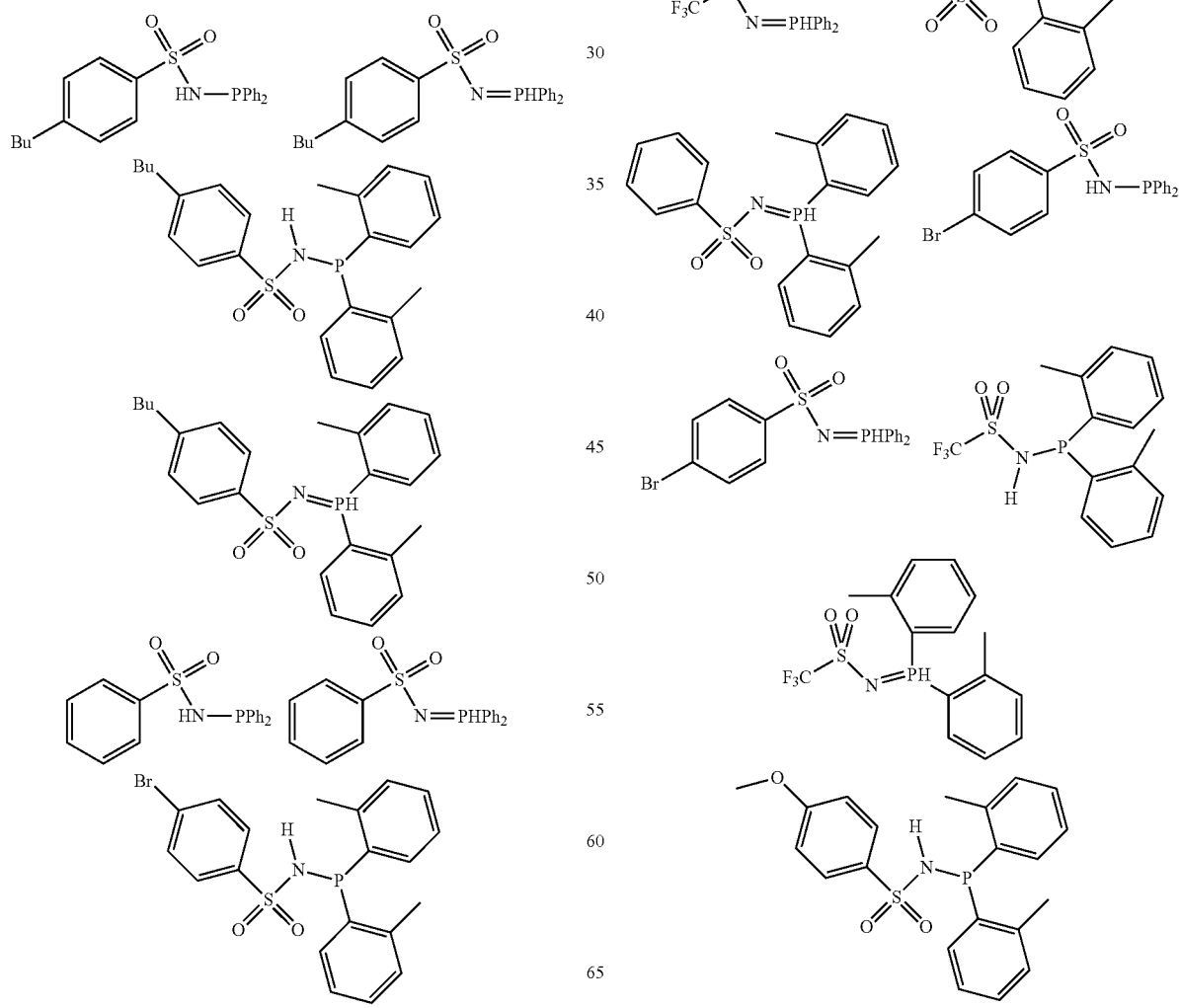

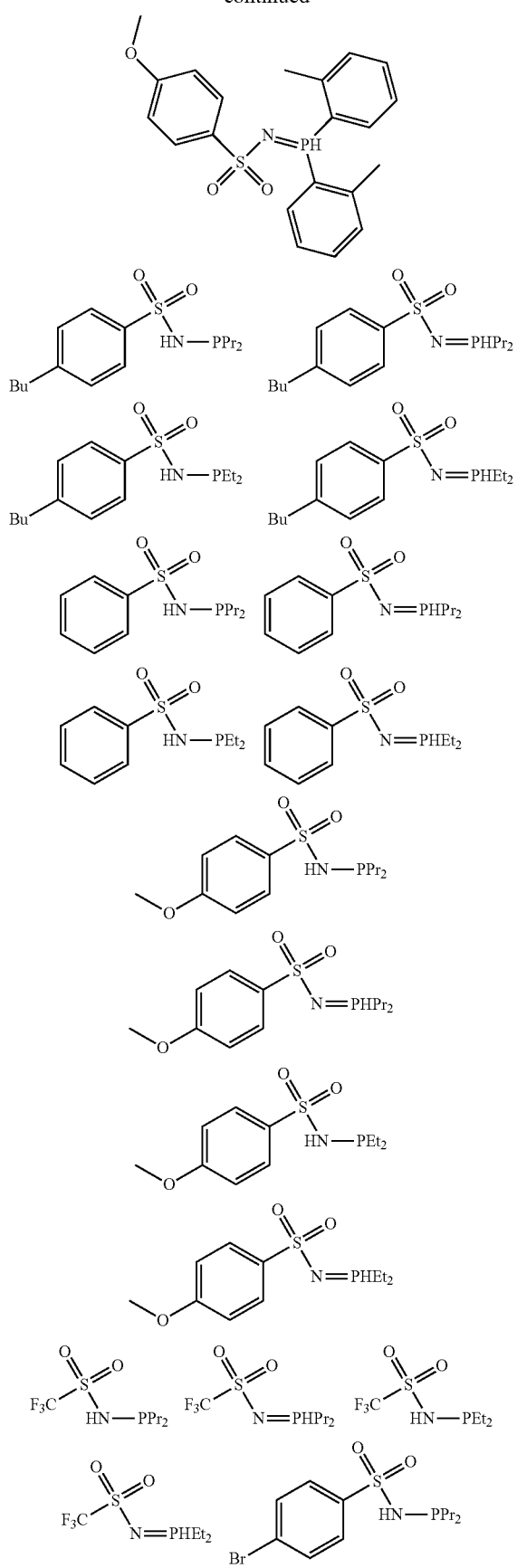
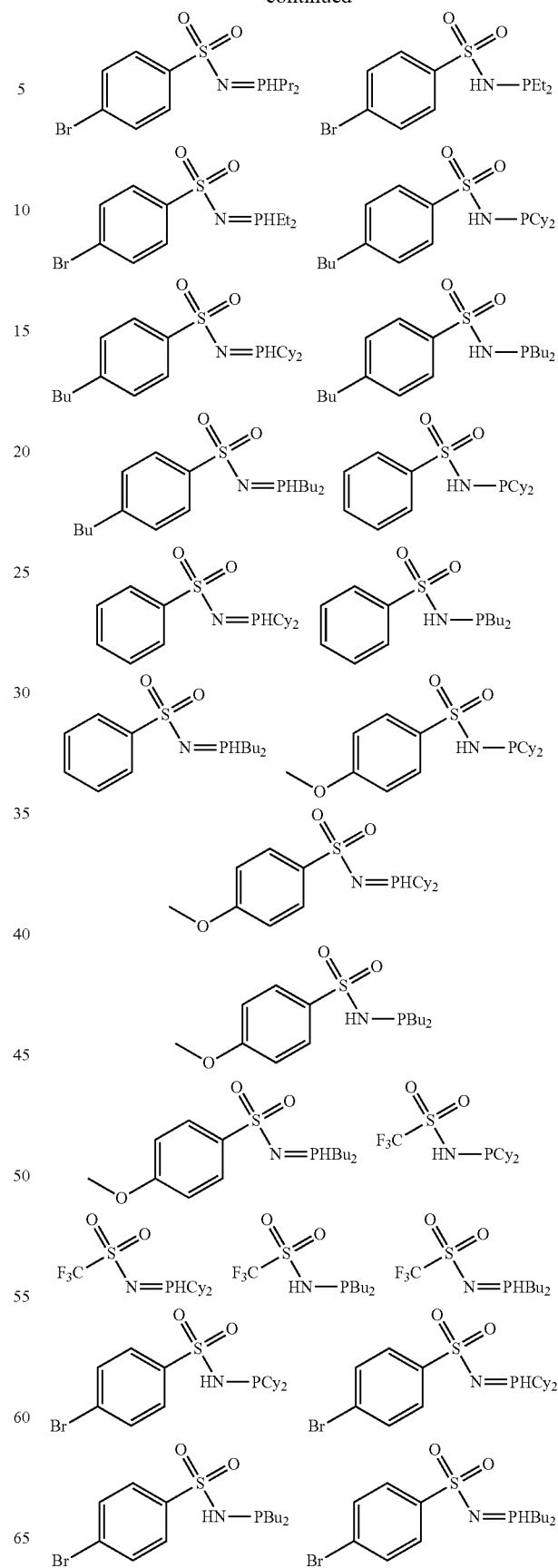

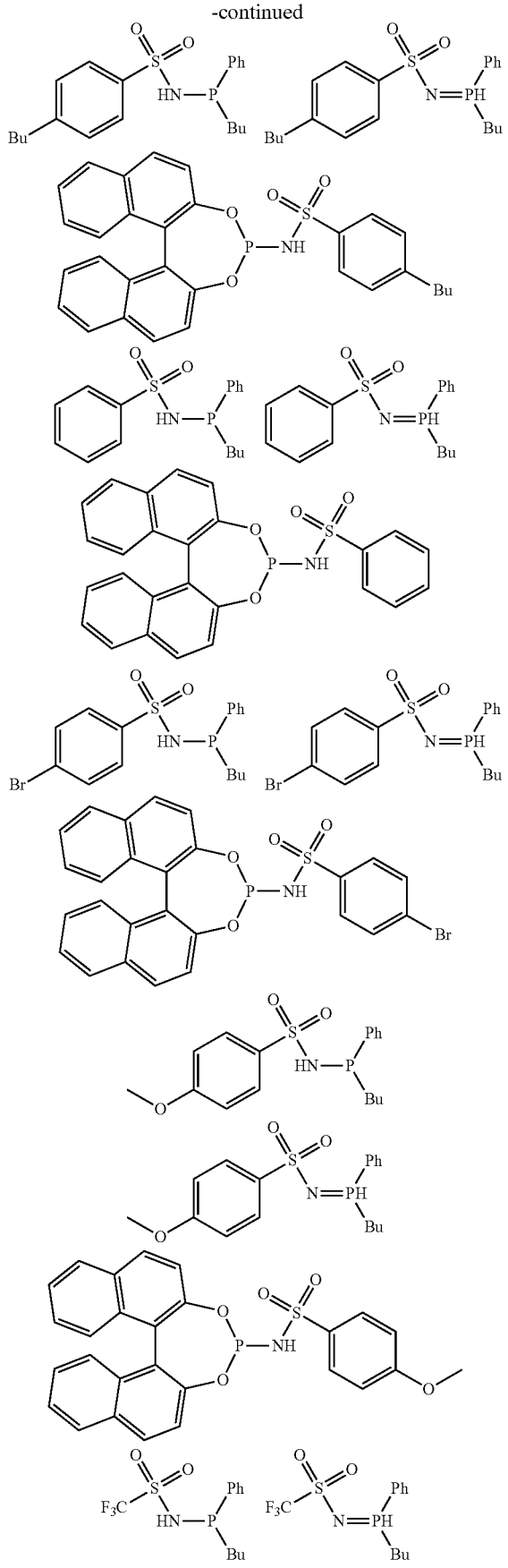

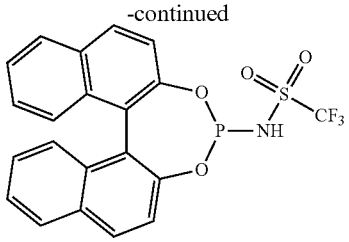

Use of Complexes with Formula (I) or (II) in a Chemical Transformation Reaction

The nickel-based complexes with formula (I) or (II) of the invention may be used as a catalyst in a chemical transformation reaction such as a hydrogenation, hydroformylation, cross-coupling or olefin oligomerization reaction. In particular, these complexes are used in a process for the oligomerization of a feed of olefins advantageously containing 2 to 10 carbon atoms.

The nickel complexes with formula (I) or (II) of the invention may be used in the form of a catalytic composition, mixed with a compound known as an activating agent. Said activating agent is advantageously selected from the group formed by tris(hydrocarbyl)aluminium compounds, chlorine-containing or bromine-containing hydrocarbylaluminium compounds, aluminium halides, aluminoxanes, organo-boron compounds, and organic compounds which are capable of donating or accepting a proton, used alone or as a mixture.

The tris(hydrocarbyl)aluminium compounds, the chlorine-containing or bromine-containing hydrocarbylaluminium compounds and the aluminium halides preferably have the general formula $Al_xR_yW_z$, in which R represents a monovalent hydrocarbon radical containing, for example, up to 12 carbon atoms such as alkyl, aryl, aralkyl, alkaryl or cycloalkyl, W represents a halogen atom selected from chlorine and bromine, for example, W preferably being a chlorine atom, x takes the value of 1 to 2, y and z taking a value of 0 to 3. Examples of compounds of this type which may be mentioned are ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), diethylaluminium chloride ($Et_2AlCl$), trimethylaluminium, tributylaluminium, tri-n-octylaluminium and triethylaluminium ($AlEt_3$).

In the case in which said activating agent is selected from aluminoxanes, said activating agent is advantageously selected from methylaluminoxane (MAO), ethylaluminoxane and modified methylaluminoxanes (MMAO). These activating agents may be used alone or as a mixture.

Preferably, said activating agent C is selected from dichloroethylaluminium ($EtAlCl_2$) and methylaluminoxane (MAO).

In the case in which said activating agent is selected from organo-boron compounds, said activating agent is preferably selected from Lewis acids of the tris(aryl)borane type, such as tris(perfluorophenyl)borane, tris(3,5-bis(trifluoromethyl)phenyl)borane, tris(2,3,4,6-tetrafluorophenyl)borane, tris(perfluoronaphtyl)borane, tris(perfluorobiphenyl)borane and their derivatives and (aryl)borates associated with a triphenylcarbenium cation, or a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate.

In the case in which said activating agent is selected from organic compounds which are susceptible of donating a proton, said activating agent is preferably selected from acids with formula HY in which Y represents an anion.

In the case in which said activating agent is selected from organic compounds which are susceptible of accepting a proton, said activating agent is preferably selected from Brönsted bases.

The solvent for the oligomerization process may be selected from organic solvents, preferably from ethers, alcohols, chlorine-containing solvents and saturated, unsaturated, aromatic or non-aromatic, cyclic or non-cyclic hydrocarbons. In particular, said solvent is selected from hexane, cyclohexane, methylcyclohexane, heptane, butane or isobutane, monoolefins or diolefins preferably containing 4 to 20 carbon atoms, cycloocta-1,5-diene, benzene, toluene, ortho-xylene, mesitylene, ethylbenzene, dichloromethane, chlorobenzene, methanol and ethanol, pure or as a mixture, and ionic liquids. In the case in which said reaction solvent is an ionic liquid, it is advantageously selected from the ionic liquids described in patents U.S. Pat. No. 6,951,831 B2 and FR 2 895 406B1.

Oligomerization is defined as the transformation of a monomer unit into a compound or mixture of compounds with general formula $C_pH_{2p}$, with $4 \leq p \leq 80$, preferably with $4 \leq p \leq 50$, more preferably with $4 \leq p \leq 26$ and highly preferably with $4 \leq p \leq 14$.

The olefins used in the oligomerization process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) such as those found in "cuts" obtained from oil refining processes such as catalytic cracking or steam cracking.

Preferably, the olefin used in the oligomerization process is ethylene.

Said olefins may be obtained from non-fossil sources such as biomass. As an example, the olefins used in the oligomerization process of the invention may be produced from alcohols, in particular by dehydration of alcohols.

The concentration of nickel in the catalytic solution is advantageously in the range $1 \times 10^{-8}$ to 1 mol/L, and preferably in the range $1 \times 10^{-6}$ to $1 \times 10^{-2}$ mol/L.

The oligomerization process is advantageously operated at a total pressure in the range between atmospheric pressure and 20 MPa, preferably in the range 0.1 to 8 MPa, and at a temperature in the range −40° C. to +250° C., preferably in the range −20° C. to 150° C.

The heat generated by the reaction can be eliminated using any means known to the skilled person.

The oligomerization process may be carried out in a closed system, in a semi-open system or continuously, with one or more reaction stages. Vigorous stirring is advantageously carried out to ensure good contact between the reagent or reagents and the catalytic system.

The oligomerization process may be carried out discontinuously. In this case, a selected volume of the solution comprising the complex of the invention is introduced into a reactor provided with the usual stirring, heating and cooling devices.

The oligomerization process may also be carried out in a continuous manner. In this case, the solution comprising the complex of the invention is injected at the same time as the olefin into a reactor stirred using conventional mechanical means or by external recirculation, and maintaining the desired temperature.

The catalytic composition is destroyed by any usual means known to the skilled person, then the reaction products as well as the solvent are separated, for example by distillation. The olefin which has not been transformed may be recycled to the reactor.

The process of the invention may be carried out in a reactor with one or more reaction stages in series, the olefinic feed and/or the catalytic composition, having been pre-conditioned, being introduced continuously, either into the first stage or into the first and any other of the stages. At the reactor outlet, the catalytic composition may be deactivated, for example by injecting ammonia and/or an aqueous solution of sodium hydroxide and/or an aqueous solution of sulphuric acid. The unconverted olefins and any alkanes optionally present in the feed are then separated from the oligomers by distillation.

The products of the present process may find an application, for example, as fuel components for automobiles, as feeds in a hydroformylation process for the synthesis of aldehydes and alcohols, as components for the chemicals, pharmaceuticals or perfumery industry and/or as feeds in a metathesis process for the synthesis of propylene, for example.

The following examples illustrate the invention without limiting its scope. The notation "Cy" represents the cyclohexyl group.

EXAMPLES

Example 1

Synthesis of Ligands and Complexes

Synthesis of Ligands L1, L3 and L4.

The synthesis of ligands L1, L3 and L4 was carried out using the method described in the literature: F. G. Terrade, *Eur. J. Inorg. Chem.* 2014, 1826-1835.

Synthesis of Complex C1

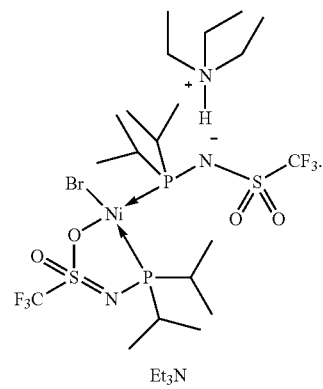

C1

The ligand L1 $F_3C$—$SO_2$—N=P($^i$Pr)$_2$H (82 mg, 0.31 mmol, 2.2 eq), NiBr$_2$ (DME) (43 mg, 0.14 mmol, 1 eq) and triethylamine (100 µL, 0.74 mmol, 5.3 eq) were suspended in a Schlenk flask with 2 mL of benzene and stirred for 10 minutes at ambient temperature. Next, the mixture was heated to 60° C. for 16 hours (h) and the solvent was then evaporated off. The red powder obtained was washed with pentane. Crystals were obtained by diffusing pentane into a toluene solution.

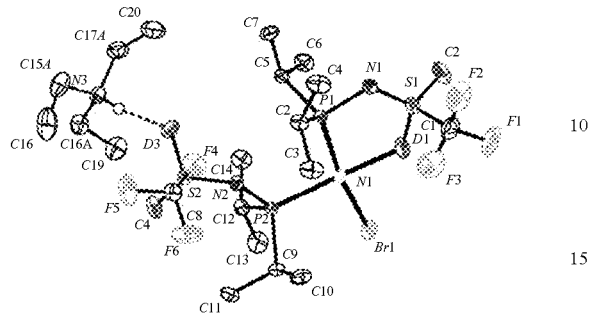

Synthesis of Complex C2

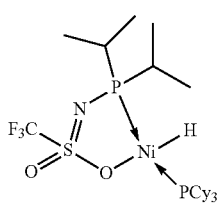

Ligand L1 ($F_3C$—$SO_2$—N=P(iPr)$_2$H, 796 mg, 3 mmol, 1 eq), Ni(COD)$_2$ (825 mg, 3 mol, 1 eq) and tricyclohexylphosphine (840 mg, 3 mmol, 1 eq) were dissolved in 30 mL of toluene. The solution was stirred until the components had dissolved, then heated to 60° C. for 3 h. The solvent was evaporated off under reduced pressure to produce a powder. After trituration and washing in pentane (3×10 mL), a yellow powder was obtained; when dried under vacuum, it corresponded to the isolated product: 694 mg, 38%.

$^{31}$P NMR (C$_6$D$_6$): 36.5 (dd, $^2J_{PP}$=232 Hz and 28.6 Hz); 103.0 (dd, $^2J_{PP}$=233 Hz and J$_{PH}$=72.9 Hz).

Synthesis of Complex C3

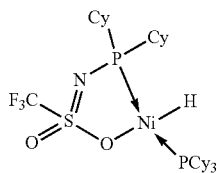

Ligand L3 (F$_3$C—SO$_2$—N=P(Cy)$_2$H, 205 mg, 0.5 mmol, 1 eq), Ni(COD)$_2$ (412 mg, 1.5 mmol, 1 eq) and tricyclohexylphosphine (420 mg, 1.5 mmol, 1 eq) were dissolved in 20 mL of toluene. The solution was stirred until the components had dissolved, then heated at 60° C. for 16 h. The solvent was evaporated off under reduced pressure to produce a powder. After trituration and washing in pentane (3×10 mL), a yellow powder was obtained (isolated: 465 mg, 45%). $^{31}$P NMR (C$_6$D$_6$): 36.6 (dd, $^2J_{PP}$=236 Hz and 67 Hz); 78.6 (dd, $^2J_{PP}$=237 Hz and J$_{PH}$=82 Hz).

Synthesis of Complex C4

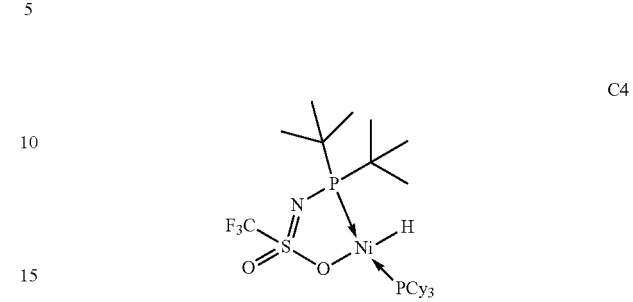

Ligand L4 (F$_3$C—SO$_2$—N=P($^t$Bu)$_2$H, 58 mg, 0.2 mmol, 1 eq), tricyclohexylphosphine (56 mg, 0.2 mmol, 1 eq) and Ni(COD)$_2$ (55 mg, 0.2 mmol, 1 eq) were placed in a Schlenk flask in 5 mL of toluene. The mixture was heated and stirred at 90° C. for 3 h. The solvent was then evaporated off to produce a solid. This solid was triturated then washed with pentane (3×5 mL) to produce a yellow solid. The product was characterized by $^{31}$P(C$_6$D$_6$) NMR: 40.4 ppm (dd, $^2J_{PP}$=235 Hz and $^2J_{PH}$=69 Hz); 120.7 ($^2J_{PP}$=235 Hz and $^2J_{PH}$=68 Hz).

Synthesis of Complex C5

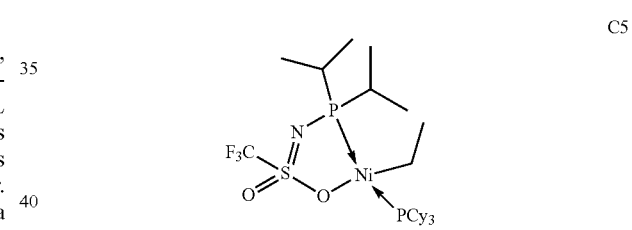

Ligand L3 (F$_3$C—SO$_2$—N=P(iPr)$_2$H, 205 mg, 0.5 mmol, 1 eq), Ni(COD)$_2$ (412 mg, 1.5 mmol, 1 eq) and tricyclohexylphosphine (420 mg, 1.5 mmol, 1 eq) were dissolved in 20 mL of toluene. The solution was stirred until the components had dissolved, then heated to 60° C. for 3 h. A stream of ethylene was passed through this solution until the colour became clear (10 minutes at ambient temperature, with stirring and at 1 bar of ethylene). The complex C5 was obtained. The product was characterized by $^{31}$P(C$_6$D$_6$) NMR: 89.6 (d, $^2J_{PP}$=245 Hz); 18.7 (d, $^2J_{PP}$=243 Hz).

Example 2

Oligomerization of Ethylene

The ethylene oligomerization reaction was evaluated with complexes C2 and C3 (10 µmoles). The results obtained are reported in Table 1.

The 250 mL reactor was dried under vacuum at 130° C. for 2 hours then pressurized with 0.5 MPa of ethylene. The temperature was dropped to 20° C., then the excess pressure of ethylene was evacuated to obtain 0.1 MPa. The solvent was added (45 mL of toluene) and the internal temperature was set (40° C.). Once the internal temperature had stabilized, the complex was introduced (10 µmol in 5 mL of toluene). Next, the reactor was pressurized with 3 MPa of ethylene. Stirring (1000 rpm) was commenced (t=0). After the pre-set reaction time, the mixture was cooled to 30° C. with stirring, the reactor was depressurized and the liquid and gas phases were analysed by gas phase chromatography (GC).

The productivity ($g_{oligo}/g_{Ni} \cdot h$) is expressed as the mass of oligomers produced (in grams) per unit mass of nickel employed per hour.

TABLE 1

Oligomerization of ethylene with different complexes

| Complex | Temperature | Mass of oligomers (g) | Reaction time (min) | Productivity $g_{oligo}/(g_{Ni} \cdot h)$ | Distribution of products (by wt)[a] | | | 1-butene[b] | 1-hexene |
|---|---|---|---|---|---|---|---|---|---|
| | | | | | $C_4$ | $C_6$ | $C_8^+$ | | |
| C2 | 40° C. | 4.6 | 90 | 1040 | 38.9 | 26.6 | 34.5 | 98.8 | 99.1 |
| C3 | 40° C. | 14.5 | 90 | 3300 | 19.5 | 21.4 | 59.1 | 99.9 | 99.0 |

[a]Determined by GC (percentage by weight of $C_4$, $C_6$ and $C_8^+$ with respect to all of the oligomers).
[b]Percentage by weight of 1-butene in the $C_4$ cut.

The above examples demonstrate that the complexes of the invention exhibit good activity in the oligomerization of ethylene.

The invention claimed is:

1. A nickel-based complex with formula (I) or with formula (II)

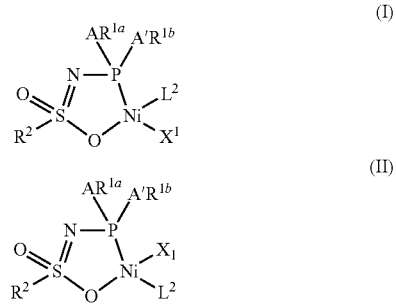

in which
the atoms P, N, S, O constitute a ligand fragment,
A and A', which may be identical or different, are independently O, S, $NR^3$ or a single bond between the phosphorus atom and a carbon atom,
the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements,
the groups $R^1$, represented in the formula by $R^{1a}$ and $R^{1b}$, with $R^{1a}$ and $R^{1b}$ being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group $R^2$ is selected from alkyl groups which may or may not be cyclic, which may or may not be substituted and which may or may not contain heteroelements, and aromatic groups which may or may not be substituted and which may or may not contain heteroelements, $L^2$ represents a Lewis base,
$X^1$ is a hydrogen atom or a halogen or a carbon atom bonded to or forming part of at least one alkyl group, which may or may not be cyclic, which may or may not be unsaturated, which may or may not be substituted and which may or may not contain heteroelements, and an aromatic group which may or may not be substituted and which may or may not contain heteroelements,
$L^2$ and $X^1$ are such that the oxidation number of the nickel is respected.

2. The complex according to claim 1, in which $L^2$ represents a phosphine of the type $P(A^1R'^{1a})(A'^1R'^{1b})(A''^1R'^{1c})$ or a phosphinamine of the type $(R'^{1a}A^1)(R'^{1b}A'^1)P-NH(R'^2)$ or $R'^{1a}A^1)(R'^{1b}A'^1)P-NH-S(O)_2(R'^2)$, in which:
$A^1$, $A'^1$ and $A''^1$, which may be mutually identical or different, are independently O, S, $NR^3$, or a single bond between the phosphorus atom and a carbon atom,
the group $R^3$ is either a hydrogen atom or an alkyl group, which may or may not be cyclic, which may or may not be substituted and which may or may not contain heteroelements, or an aromatic group which may or may not be substituted and which may or may not contain heteroelements,
the groups $R'^1$, i.e. $R'^{1a}$, $R'^{1b}$ and $R'^{1c}$, being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group $R'^2$ is selected from alkyl groups which may or may not be cyclic, which may or may not be substituted and which may or may not contain heteroelements, and aromatic groups which may or may not be substituted and which may or may not contain heteroelements.

3. The complex according to claim 1, in which the groups $R^1$ i.e. $R^{1a}$ and $R^{1b}$, which may be identical or different and which may or may not be bonded together, and the groups $R'^1$, i.e. $R'^{1a}$, $R'^{1b}$ and $R'^{1c}$, which may be identical or different and which may or may not be bonded together, are independently selected from alkyl groups containing 1 to 15 carbon atoms and aromatic groups containing 5 to 20 carbon atoms, which may or may not be substituted and which may or may not contain heteroelements.

4. The complex according to claim 3, in which the groups $R^1$, i.e. $R^{1a}$ and $R^{1b}$ which may be identical or different, which may or may not be bonded together, and the groups $R'^1$, i.e. $R'^{1a}$, $R'^{1b}$ and $R'^{1c}$, which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups, which may or may not be substituted and which may or may not contain heteroelements.

5. The complex according to claim 1, in which the groups $R^2$ and the groups $R'^2$, which may be identical or different, are independently selected from alkyl groups containing 1 to 15 carbon atoms and aromatic groups containing 5 to 20 carbon atoms, which may or may not be substituted and which may or may not contain heteroelements.

6. The complex according to claim 5, in which the groups $R^2$ and the groups $R'^2$, which may be identical or different, are independently selected from methyl, trifluoromethyl, ethyl, n-propyl, i-propyl, n-butyl, i-butyl, t-butyl, pentyl, cyclohexyl and adamantyl groups, which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain heteroelements.

7. A process for the preparation of a complex according to claim 1, comprising bringing at least one ligand comprising said ligand fragment constituted by the atoms P, N, S and O into contact with at least one precursor of nickel with an oxidation number of (0), a precursor of the group $X^1$, and optionally a Lewis base.

8. The process according to claim 7, in which the nickel precursor is selected from nickel(0) bis(cycloocta-1,5-diene), nickel(0) bis(cycloocta-1,3-diene), nickel(0) bis(cyclooctatetraene), nickel(0) bis(cycloocta-1,3,7-triene), bis(o-tolylphosphito) nickel(0)(ethylene), nickel(0) tetrakis (triphenylphosphite), nickel(0) tetrakis(triphenylphosphine) and nickel (0) bis(ethylene), used alone or as a mixture.

9. A process for the preparation of a complex according to claim 1, comprising bringing at least one ligand comprising said ligand fragment constituted by the atoms P, N, S and O into contact with at least one precursor of nickel with an oxidation number of (+II), in the presence of a reducing agent or a Brönsted base; and optionally a Lewis base.

10. The process according to claim 9, in which the nickel precursor is selected from nickel (II) chloride, nickel(II) (dimethoxyethane) chloride, nickel(II) bromide, nickel(II) (dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate, for example, nickel(II) phenates, nickel (II) acetate, nickel(II) trifluoroacetate, nickel(II) triflate, nickel(II) acetylacetonate, nickel(II) hexafluoroacetylacetonate, allylnickel(II) chloride, allylnickel(II) bromide, methallylnickel(II) chloride dimer, allylnickel(II) hexafluorophosphate, methallylnickel(II) hexafluorophosphate, biscyclopentadienyl nickel(II), bisallyl nickel(II) and bismethallyl nickel(II); in their hydrated or non-hydrated form, used alone or as a mixture.

11. A method which comprises employing a complex prepared in accordance with claim 7, as a catalyst.

12. A process for the oligomerization of a feed of olefins, comprising bringing said feed into contact with a complex prepared in accordance with claim 7, in the presence or absence of solvent.

13. The process according to claim 12, in which the complex is used as a mixture with a compound selected from the group formed by tris(hydrocarbyl)aluminium compounds, chlorine-containing or bromine-containing compounds of hydrocarbylaluminium, aluminoxanes, organoboron compounds and organic compounds which are susceptible of donating or accepting a proton, used alone or as a mixture.

14. The process according to claim 12, in which the feed comprises olefins containing in the range 2 to 10 carbon atoms.

15. The process according to claim 12, in which the reaction is an ethylene oligomerization reaction.

* * * * *